United States Patent

Oishi et al.

[11] 4,214,091
[45] Jul. 22, 1980

[54] ANTIBIOTIC NO. 2-200 AND PROCESS FOR PRODUCING THEREOF

[75] Inventors: Hideo Oishi, Sayama; Takao Noto, Machida; Yoshiharu Nawata, Kodaira; Hiroshi Okazaki, Sayama; Hiroshi Sasaki, Higashikurume; Kunio Ando, Kawasaki; Haruki Ogawa, Chofu, all of Japan

[73] Assignee: Chugai Seiyaku Kabushiki Kaisha, Tokyo, Japan

[21] Appl. No.: 944,303

[22] Filed: Sep. 21, 1978

[30] Foreign Application Priority Data

Sep. 22, 1977 [JP] Japan ............... 52-113205

[51] Int. Cl.$^2$ ............... C07D 333/32; A61K 31/38
[52] U.S. Cl. ............... 549/62; 435/117; 424/275
[58] Field of Search ............... 260/332.3 R; 195/96; 549/62

[56] References Cited

U.S. PATENT DOCUMENTS 3,051,728   8/1962   Engster ............... 260/332.3 R

Primary Examiner—Howard T. Mars
Assistant Examiner—L. Hendriksen
Attorney, Agent, or Firm—Browdy and Neimark

[57] ABSTRACT

A novel antibiotic No. 2-200 represented by the formula

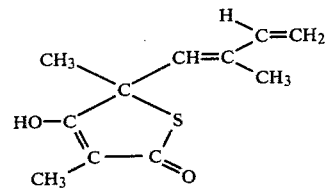

which has a broad antimicrobial spectrum and a process for producing the same by cultivating an antibiotic No. 2-200 producing microorganism of the genus Nocardia, and recovering by isolation the antibiotic No. 2-200 accumulated in the culture.

1 Claim, 4 Drawing Figures

ANTIBIOTIC NO. 2-200 AND PROCESS FOR PRODUCING THEREOF

This invention relates to a novel antibiotic No. 2-200 having a broad antimicrobial spectrum and a process for producing such antibiotic.

As a result of screening for novel antibiotics produced by microorganisms, the present inventors have found that a certain actinomycete produces and accumulates an antibiotic that strongly inhibits the growth of a mutant of Pseudomonus aeroginosa, for example, G-75, M-57740, that is sensitive to a $\beta$-lactam antibiotic. The present inventors further continued their studies and succeeded in isolating from a culture of actinomycete an effective substance as a crystal, which was subjected to X-ray diffractometry to determine its structure. The substance was found to be a novel antibiotic, which was designated No. 2-200. This invention is a development of studies based on these findings.

This invention therefore relates to an antibiotic No. 2-200 produced by a microorganism of the genus Nocardia and a process for producing said antibiotic comprising cultivating in a medium an antibiotic No. 2-200 producing microorganism of the genus Nocardia and recovering through isolation the accumulated antibiotic No. 2-200 from the culture.

Any microorganism of the genus Nocardia having the ability to produce No. 2-200 may be used in this invention. A suitable example is Nocardia sp. No. 2-200 strain isolated from a soil sample in Saitama Prefecture. The strain has been deposited on Aug. 23, 1977 under the identification number ATCC 31319 and also deposited at the Agency of Industrial Science and Technology, Research Institute under FERM-P-No. 4171.

Figure 1:
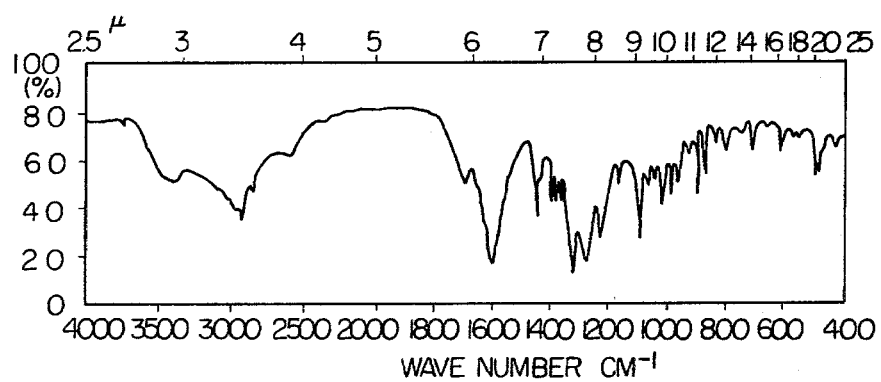
FIG. 1 shows the infrared absorption spectrum of the antibiotic No. 2-200.

Following are the bacteriological characteristics of the strain.

(1) Morphological characteristics

The substrate mycelium is branched into short aerial mycelia. A colony without aerial mycelia was yellowish brown and turned white as it developed aerial mycelia. Each aerial mycelium divided into short rods in the course of incubation; for instance, most of the aerial mycelia of cells incubated on a sucrose nitrate agar medium at 28° C. for 21 days divided into bacillus-like cells. No sporophores as found in Streptomyces sp. were observed. Almost all substrate mycelia were pleomorphic and divided into rods.

From the above morphological features, the strain was found to belong to the genus Nocardia of soft type.

(2) Observation on various media (after incubation at 28° C. for 18 days)

| Medium | Growth | Color of colony surface (Aerial mycelium) | Substrate mycelium | Soluble pigment and others |
|---|---|---|---|---|
| Trypton | moderate, part of colony precipitated, lens-like colony on liquid surface | | | |
| yeast extract (IPS-1) | | white | | none |
| yeast malt extract agar (IPS-2) | good elevated wrinkled | white, a few aerial mycelia | pale yellow orange | none |
| oatmeal agar (IPS-3) | moderate, flat | white | pale yellow orange | none |
| starch inorganic salt agar (IPS-4) | weak to moderate | white | pale yellowish brown | none starch highly hydrolyzed |
| glycerin asparagine agar (IPS-5) | weak powdery | white | pale red orange | none |
| peptone yeast extract iron agar (IPS-6) | moderate, elevated wrinkled | no aerial mycelium | pale yellowish brown | none |
| tyrosine agar (IPS-7) | good, powdery | white | pale yellowish brown | none |
| sucrose sodium nitrate agar (Waksman-1) | moderate | no aerial mycelium in the center of colony, white periphery | pale yellowish brown | none |
| glucose asparagine agar (Waksman-2) | good, powdery | white | pale yellow orange | none |
| nutrient agar (Waksman-8) | moderate, wrinkled | a few aerial mycelia white | colorless | none |
| gelatin (Waksman-19) | wrinkled precipitate, moderate | — | colorless | none strong gelatin liquefaction |
| skim milk (Waksman-14) | weak | — | — | none no coagulation or peptonization |

(3) Physiological properties
- Hydrolysis of starch +
- Tyrosinase reaction —
- Hydrolysis of gelatin +
- Coagulation and peptonization of milk —
- Formation of $H_2S$ —

The novel antibiotic No. 2-200 of this invention is produced by cultivating Nocardia sp. No. 2-200 in a liquid nutrient medium under aerobic conditions, preferably submerged conditions, as described hereinafter.

(4) Utilization of various carbohydrates (on IPS-9 medium)

| D-glucose | + | D-xylose | — | D-fructose | — |
|---|---|---|---|---|---|
| L-arabinose | ± | Inositol | — | Rhamnose | — |

| | | |
|---|---|---|
| Sucrose | + D-mannitol − | Raffinose − |

X-ray diffractometry shows that the antibiotic No. 2-200 of this invention is an entirely novel organic compound of the following plane structure:

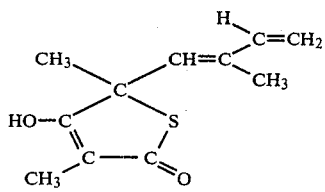

The physico-chemical properties of the antibiotic are as follows:

(1) Elemental analysis

| | C | H | S |
|---|---|---|---|
| Calculated (%) | 62.86 | 6.67 | 15.23 |
| Found (%) | 62.57 | 6.78 | 14.93 |

(2) Molecular formula $C_{11}H_{14}O_2S$ with a molecular weight of 210 as determined by mass spectrometric analysis (3) Melting point 124° to 126° C.

(4) Infrared absorption spectrum

The antibiotic has an infrared absorption spectrum as shown in FIG. 1. The more characteristic absorption bands are set forth in the table below.

| | | |
|---|---|---|
| 3400 cm$^{-1}$ brd M | 2960 cm$^{-1}$ brd M | 2925 cm$^{-1}$ M |
| 1690 cm$^{-1}$ M | 1605 cm$^{-1}$ brd VS | 1445 cm$^{-1}$ M |
| 1396 cm$^{-1}$ M | 1380 cm$^{-1}$ M | 1365 cm$^{-1}$ M |
| 1323 cm$^{-1}$ VS | 1280 cm$^{-1}$ S | 1229 cm$^{-1}$ M |
| 1169 cm$^{-1}$ M | 1090 cm$^{-1}$ S | 1068 cm$^{-1}$ M |
| 1046 cm$^{-1}$ S | 1018 cm$^{-1}$ M | 987 cm$^{-1}$ M |
| 966 cm$^{-1}$ W | 927 cm$^{-1}$ W | 900 cm$^{-1}$ M |

Figure 2:
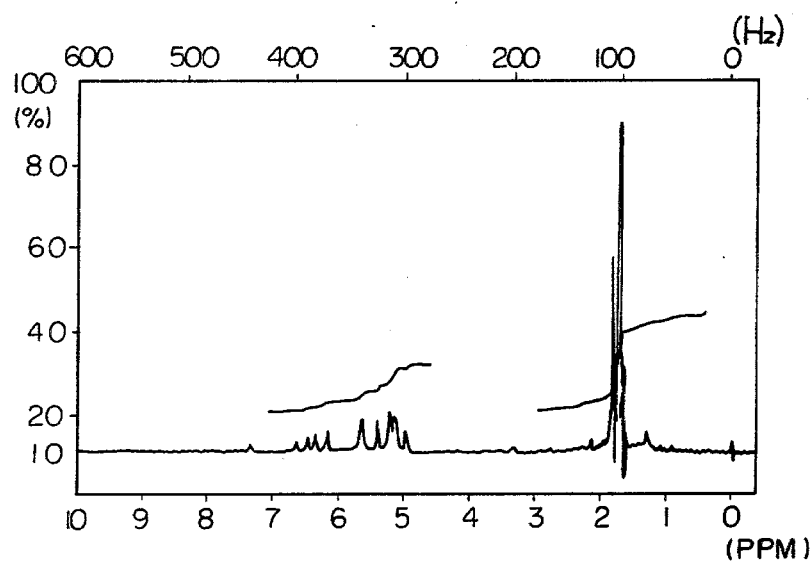
FIG. 2 shows the nuclear magnetic resonance spectrum of said antibiotic.

Notations:
VS = very strong;
S = strong;
M = medium;
W = weak;
VW = very weak;
brd = broad (5) Nuclear magnetic resonance spectrum The antibiotic has a nuclear magnetic resonance spectrum as shown in FIG. 2. The figure was obtained by spectrometry as 60 MHz using a 10% solution of the antibiotic in deuterium methanol, with tetramethyl silane (TMS) added as the internal standard.

(6) Ultraviolet absorption spectrum

Figure 3:
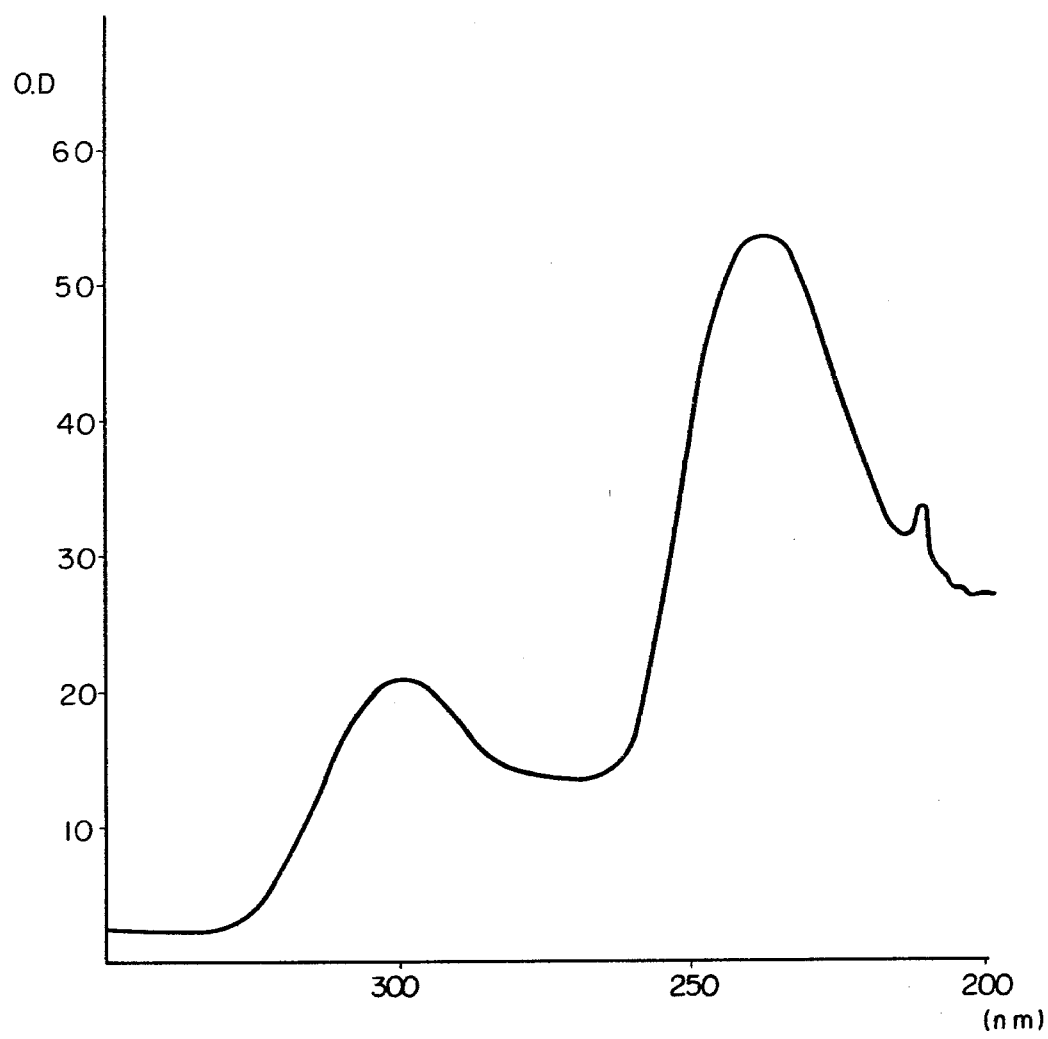
FIG. 3 shows the ultraviolet absorption spectrum of the antibiotic.

The antibiotic has an ultraviolet absorption spectrum as shown in FIG. 3. Methanol was used as the solvent. An absorption peak was observed at 237 nm and 300 nm under neutral conditions.

(7) Mass spectrum

Figure 4:
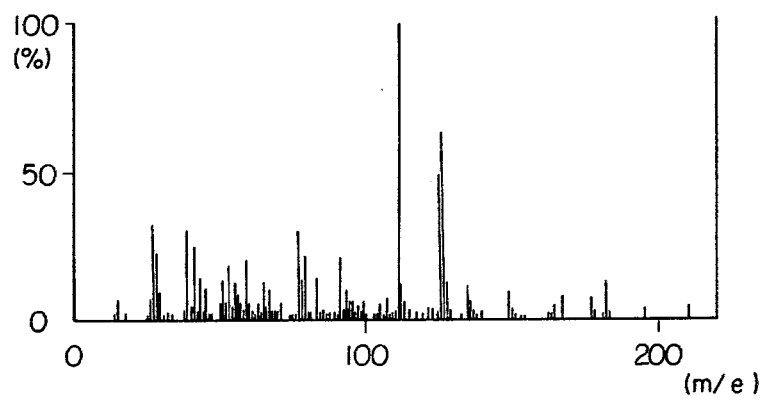
FIG. 4 shows the mass spectrum of said antibiotic.

The antibiotic has a mass spectrum as shown in FIG. 4. The peak m/e 111 is the base peak and the peak m/e 210 is the parent peak.

(8) Color reaction

Discoloration of $KMnO_4$: Positive
Nitroprusside reaction: Positive
Molisch reaction: Negative (9) Solubility in solvents

| Solvent | solubility |
|---|---|
| neutral to acidic water | slightly soluble |
| alkaline water | easily soluble |
| methanol | easily soluble |
| acetone | easily soluble |
| ethyl acetate | easily soluble |

(10) Rf on thin layer chromatography (using Kieselgel 60 F254, Art 5729, manufactured by E. Merck)

| Solvent system | Rf |
|---|---|
| benzene:acetone (3:1) | 0.3 |
| acetone | 0.8 |
| ethyl acetate | 0.5 |

The antibiotic No. 2-200 is an acidic substance which easily forms a nontoxic salt with organic or inorganic base such as ethanol amine, triethyl amine, caustic soda, caustic potash or ammonia. These salts are water soluble, and so, the antibiotic is advantageously used as an injectionable preparation.

Like other species of the genus Nocardia, Nocardia sp. No. 2-200 easily undergoes a change in its characteristics; for example, it mutates easily by artificial mutating means such as ultraviolet rays, X-rays, radioactive rays, mutation inducer. Any mutants thus produced can be employed in the process of this invention so long as they have the ability to produce and accumulate the antibiotic No. 2-200.

According to the process of this invention, either solid cultivation or liquid cultivation may be used for cultivating Nocardia sp. No. 2-200 so as to produce and accumulate the antibiotic No. 2-200 in the medium. Any of stationary cultivation, stirring cultivation, shaken cultivation and aeration cultivation may be used for liquid cultivation; aeration cultivation under stirring may advantageously be used for mass production.

The formulation of the medium conventionally used for cultivation of actinomycetes may be employed for the purpose of this invention. For instance, carbohydrates such as starch and glucose, alcohols such as glycerin, methanol and ethanol, aliphatic acids such as acetic acid, linoleic acid and palmitic acid, and oils such as soybean oil, cottonseed oil and fish oil may be used singly or in a mixture as a carbon source. Organic nitrogen sources such as soybean powder, cottonseed powder, corn steep liquor (hereunder C.S.L.), yeast and meat extract, or inorganic nitrogen sources such as inorganic ammonium salts typified by ammonium sulfate, ammonium nitrate, ammonium chloride, and ammonium phosphate may be used. Inorganic salts usually required for cultivation of actinomycetes such as calcium carbonate, sodium chloride, sodium nitrate, potassium chloride, potassium primary phosphate and sodium secondary phosphate may be used alone or in proper combination. If desired, heavy metal salts, vitamins as well as anti-foaming agent or surface active agent such as silicone oil or polyalkylene glycol ether may be used. According to the process of this invention, the medium containing these nutrient sources is inoculated with Nocardia sp. No. 2-200 for cultivation. The cultivation temperature is properly selected from the optimum temperature range for the growth of Nocardia sp. No. 2-200; it is normally from 15° to 35° C., preferably from 24° to 32° C. Cultivation may continue until maximum accumulation of the antibiotic No. 2-200 is obtained; normally, such period ranges from 12 to 168 hours, preferably from 24 to 144 hours.

The antibiotic No. 2-200 thus produced in the culture is isolated and recovered by a method conventionally employed for recovering the metabolic product produced by a microorganism. The antibiotic of this invention is acidic and can be recovered by controlling the pH of the filtrate so as to change the partition coefficient between water and an organic solvent immiscible with water such as ethyl acetate or ether. More specifically, Nocardia sp. No. 2-200 is isolated from the culture filtrate that contains a major portion of the antibiotic No. 2-200; the filtrate is adjusted to pH 3 with a mineral acid, for example, hydrochloric acid, and extracted once with an equal amount of ethyl acetate, upon which the antibiotic No. 2-200 is transferred to the ethyl acetate layer. Vacuum concentration of the ethyl acetate layer produces an antibiotic-containing syrup. The syrup thus obtained is purified by column chromatography on Silica Gel G (product of E. Merck) and Sephadex LH-20 (product of Pharmacia) using *Pseudomonas aeroginosa* G-75, M57740 as the test organism. A pale yellow needle crystal of the antibiotic No. 2-200 is produced.

As shown in Table 1, the antibiotic No. 2-200 exhibits antibacterial activity to gram negative bacteria, but it has no appreciable toxicity against mammals. A small amount of the antibiotic is sufficient to inhibit the growth of various pathogenic bacteria; one significant advantage is that it exhibits particularly strong antibacterial activity to bacteria of genus Salmonella and Serratia. The antibiotic has an extremely weak toxicity, and presents no delayed toxicity. Therefore, the antibiotic No. 2-200 of this invention is extremely advantageous as an agent for curing or preventing diseases due to infection with microorganisms in humans or animals.

Table 1

| Minimum inhibitory concentration (MIC) for gram negative bacteria | | |
|---|---|---|
| Microorganism | MIC (μg/ml) No. 2-200 | Ceftezole |
| *Bacteroides fragilis* V-6 | 3.12 | 100 |
| *Bacteroides fragilis* V-7 | 12.5 | 25 |
| *Bacteroides fragilis* V-8 | 6.25 | >100 |
| *Fusobacterium glutinosum* 1006 | 100 | 6.25 |
| *Fusobacterium necroforum* S-45 | 3.12 | — |

Note: incubated at 37° C. for 40 hours on GAM agar medium (product of Nippon Seiyaku) using anaerobic incubator. Inoculated with $10^6$/ML.

EXAMPLE 1

A 100 ml of medium comprising 3% of glucose, 1% of dry bonillon (product of Eiken Kagaku), 0.2% of yeast extract and 0.2% of calcium carbonate in water was placed in each of 500 ml conical flasks and sterilized. The medium was inoculated with spores of Nocardia sp. No. 2-200 (deposited at Agency of Industrial Science and Technology, Research Institute, under the identification number FERM-P-No. 4171), and subjected to shake cultivation on a rotary shaker at 28° C. for 4 days. A 400 ml of the media was transferred to a 30 liter stainless steel jar fermentor charged with 20 l of a sterile medium comprising 1% of glucose, 2% of starch, 2% of C.S.L., 0.1% of dry yeast and 0.2% of calcium carbonate (pH 6.5 before sterilization) in water, and subjected to incubation at 28° C. for 72 hours with agitation (400 rpm) and air supplied at 10 l/min.

EXAMPLE 2

Nocardia sp. No. 2-200 was incubated on a liquid medium according to the same manner as used in Example 1. The microorganism was isolated from the medium using a centrifugal dehydrator precoated with Radiolite-800 (product of Showa Kagaku). About 18 l of the filtrate was adjusted to pH 3 with dilute hydrochloric acid. The filtrate thus controlled for pH was intimately admixed with an equal amount of ethyl acetate to extract the antibiotic No. 2-200. The turbid mixture was filtered with Radiolite-800, and the filtrate was left standing until it separated into two layers. The lower water layer was discarded whereas the upper ethyl acetate layer was recovered, dehydrated with anhydrous sodium sulfate and concentrated in vacuo to obtain an oily substance that contained the antibiotic No. 2-200.

EXAMPLE 3

An oily substance produced by repeating the procedure of Example 2 was added to the upper end of a column prepared by suspending 200 g of Silica Gel in benzene, and the column was eluted with 2 l of a solvent mixture of benzene and acetone (95:5) to remove the impurities. The column was further eluted with 2 l of a solvent mixture of benzene and acetone (9:1), and the elute was recovered in 15 ml fractions. The fractions having antibacterial activity against *Pseudomonas aeruginosa* G-75, M57740 were combined and concentrated to give 7 g of an oily crude antibiotic No. 2-200.

EXAMPLE 4

An oily substance containing the antibiotic No. 2-200 produced by repeating the procedure of Example 3 was added to the upper end of a column prepared by suspending 75 g of Sephadex LH-20 in a benzene/acetone mixture (9:1), and eluted with 4 l of the same solvent. The eluate was recovered in 15 ml fractions and the fractions exhibiting antibacterial activity against *Pseudomonas aeruginosa* G-75, M57740 were combined and concentrated in vacuo. The pale yellow oily product obtained was dried in vacuo in a desiccator to produce a crude crystal. The crystal was dissolved in a solvent mixture of benzene and acetone (9:1) under heating and recrystallized in a refrigerator. The yield was 2 g.

EXAMPLE 5

The crystal of the antibiotic No. 2-200 obtained in Example 4 had an antibacterial spectrum as shown in Table 2. The test organisms were incubated by agar plate dilution method at 37° C. for 24 hours, after which their growth was observed. The test organisms were incubated on an NB medium (product of Eiken Kagaku) at 37° C. overnight, and each culture obtained was diluted $10^3$- to $10^4$-fold and stamped on an agar plate. The following agar plate media were used:
  NA: nutrient agar (product of Eiken Kagaku)
  NA+G6P: glucose-6-phosphoric acid (50 μg/ml) plus nutrient agar
  Anti-3A: antibiotic medium No. 3 agar (product of Difco)
  MHA: Mueller Hinton Agar (product of Eiken Kagaku)

Table 2

Antibacterial spectrum of antibiotic No. 2-200

| Test organism | Minimum inhibitory concentration (μg/ml) | | | |
|---|---|---|---|---|
| | NA | NA + G6P | Anti-3A | MHA |
| Bacillus subtilis PCI-219 | 50 | 50 | 50 | 50 |
| Bacillus cereus | 50 | 50 | 50 | 50 |
| Bacillus thuringensis | 50 | 25 | 50 | 50 |
| Sarcina lutea | 12.5 | 12.5 | 12.5 | 25 |
| Staphylococcus epidermidis T0-3 | 50 | 50 | 100 | 50 |
| | 50 | 50 | 100 | 50 |
| Staphylococcus aureus 209P | >50 | ≧50 | '25 | 50 |
| Staphylococcus aureus 222 | >400 | ≧400 | >400 | 100 |
| Staphylococcus aureus JU-5 | >400 | ≧400 | >400 | 100 |
| Staphylococcus aureus A-5 | 50 | 25 | 25 | 50 |
| Escherichia coli NIHJ | 200 | 100 | 200 | 50 |
| Escherichia coli No. 9 | 50 | 50 | 100 | 50 |
| Salmonella enteritidis T-1 | 6.25 | 6.25 | 3.12 | 3.12 |
| Salmonella typhi TANAKA | 12.5 | 12.5 | 12.5 | 3.12 |
| Salmonella paratyphi A | 50 | 50 | 50 | 3.12 |
| Klebsiella pneumoniae 3K25 | 200 | 100 | 50 | 50 |
| Klebsiella pneumoniae 15c | 100 | 100 | 50 | 12.5 |
| Shigella flexneri 2b | 6.25 | 6.25 | 3.12 | 1.56 |
| Shigella sonnei | 100 | 100 | 100 | 50 |
| Serratia marrcescens FU-111 | 50 | 50 | 25 | 6.25 |
| Serratia marrcescens T-50 | 50 | 50 | 12.5 | 1.56 |
| Pseudomonas aeruginosa J-272 | >400 | >400 | >400 | >400 |
| Pseudomonas aeruginosa G-75 | 6.25 | 6.25 | 6.25 | 6.25 |
| Pseudomonas aeruginosa M57740 | 1.56 | 1.56 | 1.56 | ≦0.78 |
| Proteus mirabilis 1287 | 50 | 50 | 50 | 50 |
| Proteus mirabilis 9' | 50 | 50 | 100 | 200 |

EXAMPLE 6

The crystal of the antibiotic No. 2-200 obtained in Example 4 was floated in sterile distilled water, mixed with 5% caustic soda to adjust the pH to 7.0, and dissolved to make a solution. The solution was administered to 5-week-old ddY male mice to examine its actuate toxicity as well as delayed toxicity. During 10 days that followed the administration, the weight of each mouse, its food intake and water intake were measured. The median lethal dose ($LD_{50}$) upon single administration was 705 mg/kg for intravenous injection, and 810 mg/kg for intraperitoneal injection. The antibiotic was entirely free from delayed toxicity.

We claim:

1. An antibiotic No. 2-200 of the formula:

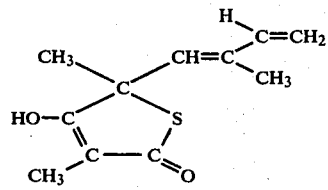

* * * * *